United States Patent
Yamaguchi

(10) Patent No.: US 8,465,417 B2
(45) Date of Patent: Jun. 18, 2013

(54) ENDOSCOPE SYSTEM

(75) Inventor: Seiji Yamaguchi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1200 days.

(21) Appl. No.: 12/273,071

(22) Filed: Nov. 18, 2008

(65) Prior Publication Data

US 2009/0137868 A1  May 28, 2009

(30) Foreign Application Priority Data

Nov. 22, 2007 (JP) ................................. 2007-303349

(51) Int. Cl.
- A61B 1/018 (2006.01)
- A61B 1/0638 (2006.01)
- A61B 1/07 (2006.01)
- A61B 1/05 (2006.01)
- H04N 5/33 (2006.01)

(52) U.S. Cl.
USPC ........... 600/113; 600/160; 600/180; 600/181; 348/216.1

(58) Field of Classification Search
USPC ................ 600/113, 160, 180, 181; 348/216.1
See application file for complete search history.

(56) References Cited

U.S. PATENT DOCUMENTS

| | | | |
|---|---|---|---|
| 5,196,928 A * | 3/1993 | Karasawa et al. | 348/65 |
| 7,585,276 B2 * | 9/2009 | Itoi | 600/180 |
| 2009/0027489 A1 * | 1/2009 | Takemura | 348/65 |

FOREIGN PATENT DOCUMENTS

| | | |
|---|---|---|
| JP | 2000-356749 A | 12/2000 |
| JP | 2001-128992 A | 5/2001 |
| JP | 2006-061214 | 3/2006 |
| JP | 2007-282965 A | 11/2007 |

OTHER PUBLICATIONS

Japanese Office Action dated Jul. 10, 2012 issued in counterpart Japanese Patent Application No. 2007-303349.

* cited by examiner

Primary Examiner — Philip R Smith
Assistant Examiner — Rynae Boler
(74) Attorney, Agent, or Firm — Scully, Scott, Murphy & Presser, P.C.

(57) ABSTRACT

An endoscope system of the invention includes: a first endoscope capable of picking up an image of a subject; a first illuminating section capable of emitting first illuminating light; a second endoscope capable of picking up an image of the subject illuminated by the first light from a direction different from the first endoscope; a second illuminating section capable of emitting second illuminating light; a video signal processing section for generating a video signal based on a signal picked-up by the second endoscope; a display section for displaying an image of the subject obtained by the video signal processing section; an emphasis instructing section for instructing an emphasis on an image obtained based on the first light; and an emphasis control section for controlling to emphasize the subject image obtained based on the first light according to an operation of the emphasis instructing section.

2 Claims, 7 Drawing Sheets

ENDOSCOPE SYSTEM

This application claims benefit of Japanese Application No. 2007-303349 filed on Nov. 22, 2007, the contents of which are incorporated by this reference.

BACKGROUND OF THE INVENTION

1. Field of the Invention

The present invention relates to an endoscope system, and more particularly, to an endoscope system capable of observing a desired target region by using two endoscopes.

2. Description of the Related Art

Conventionally, endoscope systems including endoscopes or the like have been widely used in an industrial field, a medical field or the like. In particular, endoscope systems in a medical field are mainly used for the purpose of observing various organs in a living body. Japanese Patent Application Laid-Open Publication No. 2006-61214 proposes an operation system as a system having a configuration equivalent to the endoscope system described above, for example.

To be more specific, Japanese Patent Application Laid-Open Publication No. 2006-61214 describes an operation system including a rigid endoscope inserted into an abdomen cavity through a trocar and a flexible endoscope inserted into a tube cavity such as a large intestine as an example of a system capable of observing a desired target region by using two endoscopes.

SUMMARY OF THE INVENTION

An endoscope system according to the present invention includes: a first endoscope having a first image pickup section capable of picking up an image of a subject; a first illuminating section capable of emitting a first illuminating light for illuminating the subject, the image of which is picked up by the first image pickup section; a second endoscope having a second image pickup section capable of picking up an image of the subject illuminated by the first illuminating light from a direction different from that of the first image pickup section; a second illuminating section capable of emitting a second illuminating light for illuminating the subject, the image of which is picked up by the second image pickup section; a video signal processing section for the second endoscope for generating a video signal for the second endoscope based on a signal picked up by the second image pickup section; a display section for the second endoscope for displaying an image of the subject obtained based on the video signal processing section for the second endoscope; an emphasis instructing section for instructing an emphasis on an image obtained by the first illuminating light; and an emphasis control section for performing control such that the image of the subject obtained based on the first illuminating light is emphasized in the image of the subject displayed on the display section for the second endoscope according to an operation of the emphasis instructing section.

An endoscope system according to the present invention includes: a first endoscope having a first image pickup section capable of picking up an image of a subject; a first illuminating section capable of emitting a first illuminating light for illuminating the subject, the image of which is picked up by the first image pickup section; a second endoscope having a second image pickup section capable of picking up an image of the subject illuminated by the first illuminating light from a direction different from that of the first image pickup section; a second illuminating section capable of emitting a second illuminating light for illuminating the subject, the image of which is picked up by the second image pickup section; a video signal processing section for the second endoscope for generating a video signal for the second endoscope based on a signal picked up by the second image pickup section; a display section for the second endoscope for displaying an image of the subject obtained based on the video signal processing section for the second endoscope; an emphasis instructing section for instructing an emphasis on an image obtained by the first illuminating light; and an emphasis control section for controlling the first illuminating section such that the image of the subject obtained based on the first illuminating light is emphasized in the image of the subject displayed on the display section for the second endoscope according to an operation of the emphasis instructing section.

An endoscope system according to the present invention includes: a first endoscope having a first image pickup section capable of picking up an image of a subject; a first illuminating section capable of emitting a first illuminating light for illuminating the subject, the image of which is picked up by the first image pickup section; a second endoscope having a second image pickup section capable of picking up an image of the subject illuminated by the first illuminating light from a direction different from that of the first image pickup section; a second illuminating section capable of emitting a second illuminating light for illuminating the subject, the image of which is picked up by the second image pickup section; a video signal processing section for the second endoscope for generating a video signal for the second endoscope based on a signal picked up by the second image pickup section; a display section for the second endoscope for displaying an image of the subject obtained based on the video signal processing section for the second endoscope; an emphasis instructing section for instructing an emphasis on an image obtained by the first illuminating light; and an emphasis control section for controlling the second illuminating section such that the image of the subject obtained based on the first illuminating light is emphasized in the image of the subject displayed on the display section for the second endoscope according to an operation of the emphasis instructing section.

An endoscope system according to the present invention includes: a first endoscope having a first image pickup section capable of picking up an image of a subject; a first illuminating section capable of emitting a first illuminating light for illuminating the subject, the image of which is picked up by the first image pickup section; a second endoscope having a second image pickup section capable of picking up an image of the subject illuminated by the first illuminating light from a direction different from that of the first image pickup section; a second illuminating section capable of emitting a second illuminating light for illuminating the subject, the image of which is picked up by the second image pickup section; a video signal processing section for the second endoscope for generating a video signal for the second endoscope based on a signal picked up by the second image pickup section; a display section for the second endoscope for displaying an image of the subject obtained based on the video signal processing section for the second endoscope; an emphasis instructing section for instructing an emphasis on an image obtained by the first illuminating light; and an emphasis control section for controlling the video signal processing section for the second endoscope such that the image of the subject obtained based on the first illuminating light is emphasized in the image of the subject displayed on the display section for the second endoscope according to an operation of the emphasis instructing section.

DETAILED DESCRIPTION OF THE PREFERRED EMBODIMENTS

In the following, embodiments of the present invention will be described with reference to the drawings.

First Embodiment

Figure 1:
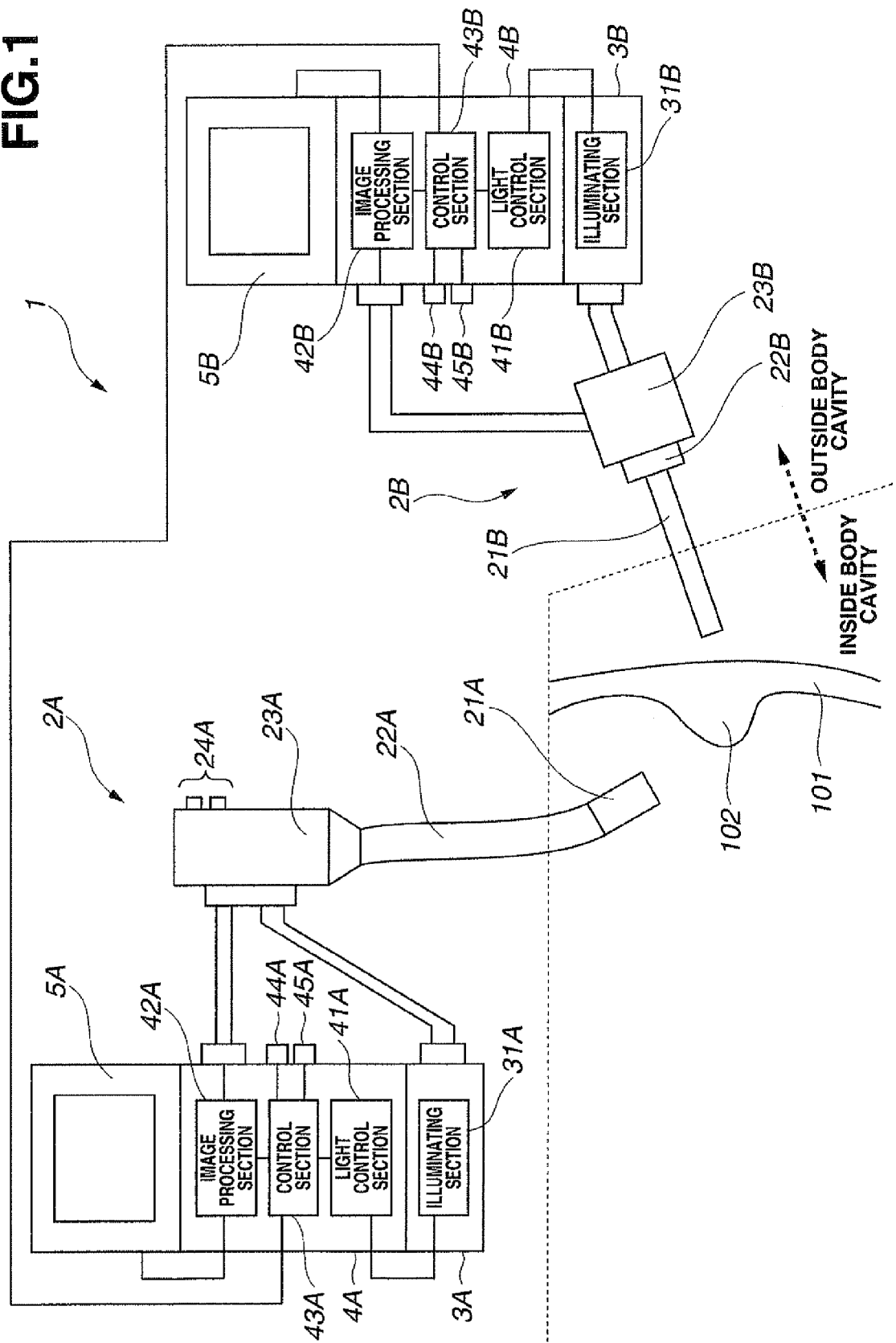
FIG. 1 illustrates a configuration example of a main portion of an endoscope system according to an embodiment of the present invention.
Figure 2:
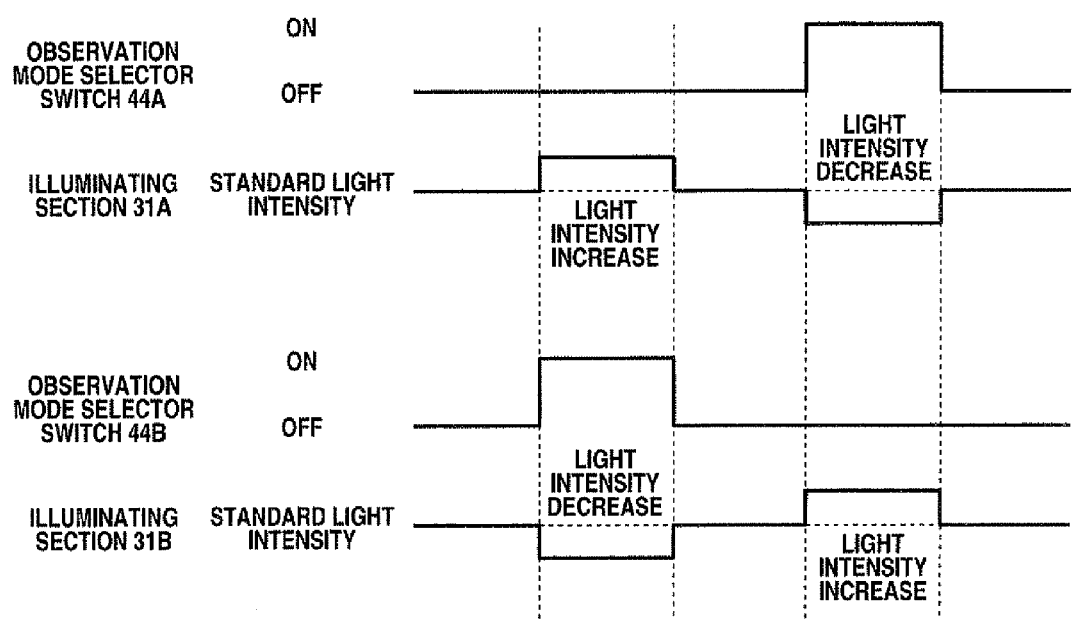
FIG. 2 illustrates an example of an operating state of each illuminating section when each observation mode selector switch is turned ON/OFF according to a first embodiment.
Figure 3:
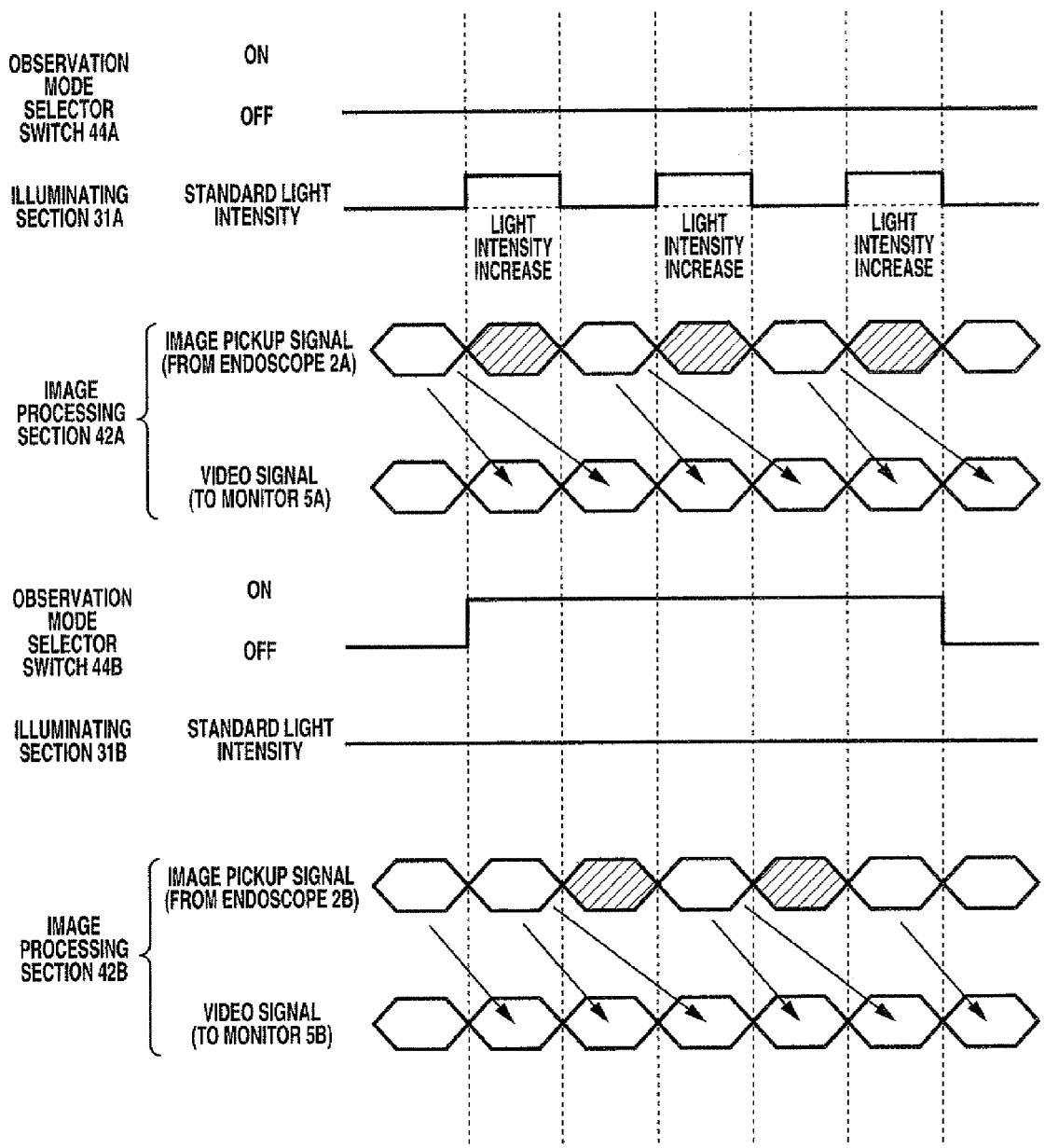
FIG. 3 illustrates an example of an operating state of each illuminating section and each image processing section when one of observation mode selector switches is turned ON according to the first embodiment.
Figure 4A:
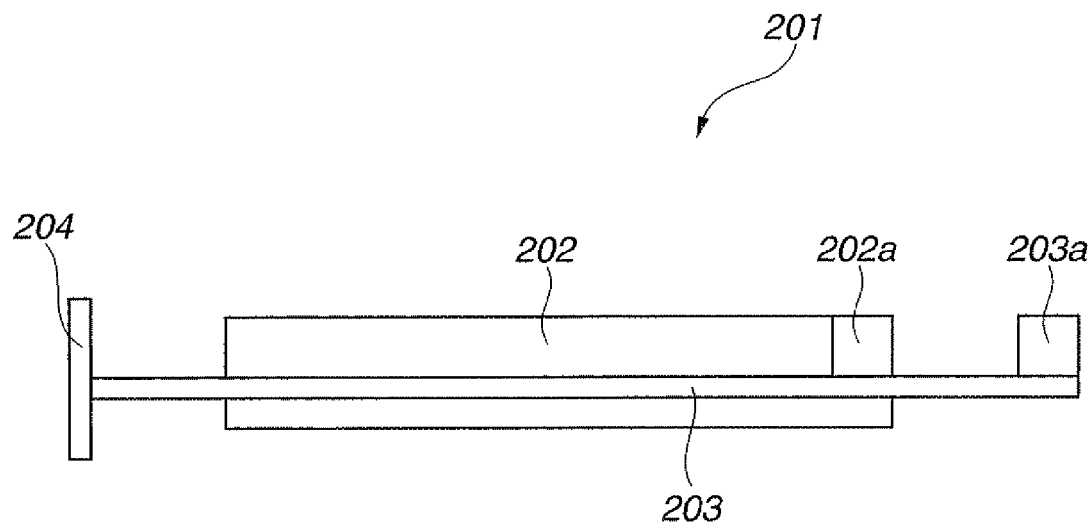
FIG. 4A illustrates a configuration example of an illuminating treatment instrument that can be used in the endoscope system in FIG. 1.
Figure 4B:
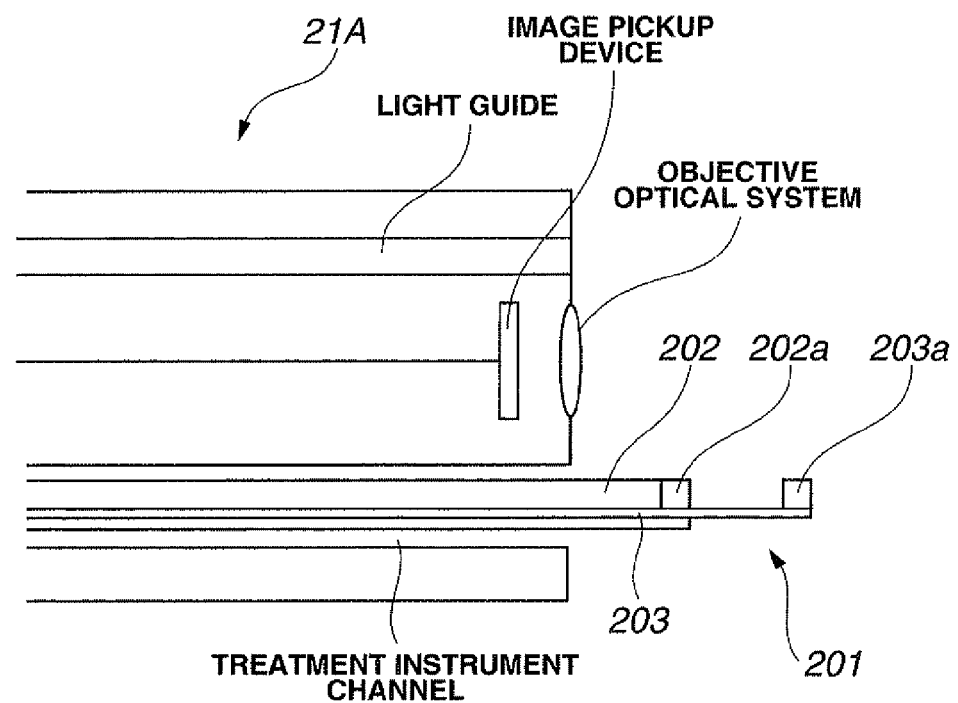
FIG. 4B illustrates an example in which each light source section of the illuminating treatment instrument in FIG. 4A is projected from a distal end portion of an endoscope.

FIGS. 1 to 4B are related to a first embodiment of the present invention. FIG. 1 illustrates a configuration example of a main portion of an endoscope system according to an embodiment of the present invention. FIG. 2 illustrates an example of an operating state of each illuminating section when each observation mode selector switch is turned ON/OFF according to the first embodiment. FIG. 3 illustrates an example of an operating state of each illuminating section and each image processing section when one of observation mode selector switches is turned ON according to the first embodiment. FIG. 4A illustrates a configuration example of an illuminating treatment instrument that can be used in the endoscope system in FIG. 1. FIG. 4B illustrates an example in which each light source section of the illuminating treatment instrument in FIG. 4A is projected from a distal end portion of an endoscope.

As shown in FIG. 1, an endoscope system 1 in the present embodiment includes an endoscope 2A that can be inserted into a tube cavity in a body cavity through a mouth or the like and picks up an image of a subject from one side of a body cavity wall 101 in the body cavity to output the picked-up image of the subject as an image pickup signal, a light source device 3A for supplying the endoscope 2A with an illuminating light for illuminating at least a visual field area of the endoscope 2A, a processor 4A for generating and outputting a video signal corresponding to the image pickup signal from the endoscope 2A and controlling the light source device 3A, and a monitor 5A for displaying an image of the subject corresponding to the video signal outputted from the processor 4A.

As shown in FIG. 1, the endoscope system 1 in the present embodiment further includes an endoscope 2B that can be inserted into a body cavity through an unillustrated trocar or the like and picks up an image of the subject from the other side of the body cavity wall 101 in the body cavity to output the picked-up image of the subject as an image pickup signal, a light source device 3B for supplying the endoscope 2B with an illuminating light for illuminating at least a visual field area of the endoscope 2B, a processor 4B for generating and outputting a video signal corresponding to the image pickup signal from the endoscope 2B and controlling the light source device 3B, and a monitor 5B for displaying an image of the subject corresponding to the video signal outputted from the processor 4B.

The endoscope 2A includes a distal end portion 21A in which an unillustrated image pickup section for picking up an image of a subject within a visual field of an objective optical system disposed at the distal end portion by an image pickup device, and outputting the image as an image pickup signal is provided, an elongated insertion portion 22A having flexibility and connected to a back side of the distal end portion 21A, and an operation portion 23A connected to a back end side of the insertion portion 22A. Also, a scope switch group 24A including a plurality of switches capable of giving various instructions or the like to the endoscope 2A and (or) the processor 4A is provided in the operation portion 23A. Moreover, an unillustrated light guide for guiding the illuminating light supplied from the light source device 3A from the operation portion 23A to a distal end surface of the distal end portion 21A is inserted into the endoscope 2A.

The light source device 3A includes an unillustrated lamp for emitting a white light as the illuminating light, for example, and an illuminating section 31A having an unillustrated aperture capable of increasing and decreasing a light intensity of the illuminating light. The illuminating section 31A adjusts the light intensity of the illuminating light supplied from the lamp to the endoscope 2A by increasing or decreasing an aperture value of the aperture based on the control of the processor 4A, for example.

The processor 4A includes a light control section 41A for controlling the light intensity of the illuminating light supplied from the light source device 3A to the endoscope 2A, an image processing section 42A having an unillustrated frame memory and generating and outputting a video signal corresponding to the image pickup signal outputted from the endoscope 2A, a control section 43A, for example, for controlling the light control section 41A and the image processing section 42A, an observation mode selector switch 44A for giving the control section 43A an instruction to switch an observation mode of the processor 4A to either a normal observation mode or a transmitted light observation mode, and a transmitted light intensity adjusting switch 45A for giving the control section 43A an instruction to adjust the light intensity of the illuminating light in the transmitted light observation mode.

The control section 43A outputs to the processor 4B an ON-OFF signal for indicating whether the observation mode selector switch 44A is ON or OFF based on an output state of the instruction from the observation mode selector switch 44A.

On the other hand, the endoscope 2B includes a rigid endoscope 21B for transmitting an image of a subject within a visual field of an objective optical system disposed at a distal end portion by a transmission optical system, an eye piece portion 22B including an eyepiece optical system allowing a user to recognize the image of the subject transmitted by the transmission optical system with naked eyes, and a camera head 23B for picking up an image of the subject image outputted through the eyepiece optical system by an image pickup device and outputting the image as an image pickup signal. Also, an unillustrated light guide for guiding the illuminating light supplied from the light source device 3B from the camera head 23B to a distal end surface of the rigid endoscope 21B is inserted into the endoscope 2B.

The light source device 33 includes an unillustrated lamp for emitting a white light as the illuminating light, for example, and an illuminating section 31B having an unillustrated aperture capable of increasing and decreasing a light intensity of the illuminating light. The illuminating section 31B adjusts the light intensity of the illuminating light supplied from the lamp to the endoscope 2B, for example, by increasing or decreasing an aperture value of the aperture, based on the control of the processor 4B.

The processor 4B includes a light control section 41B for controlling the light intensity of the illuminating light supplied from the light source device 3B to the endoscope 2B, an image processing section 42B having an unillustrated frame memory and generating and outputting a video signal corresponding to the image pickup signal outputted from the endoscope 2B, a control section 43B, for example, for controlling the light control section 41B and the image processing section 42B, an observation mode selector switch 44B for giving the control section 43B an instruction to switch an observation mode of the processor 4B to either a normal observation mode or a transmitted light observation mode, and a transmitted light intensity adjusting switch 45B for giving the control section 43B an instruction to adjust the light intensity of the illuminating light in the transmitted light observation mode.

The control section 43B outputs to the processor 4A an ON-OFF signal for indicating whether the observation mode selector switch 44B is ON or OFF based on an output state of the instruction from the observation mode selector switch 44B.

Next, the action of the endoscope system 1 of the present embodiment will be described.

First, a user connects respective sections of the endoscope system 1 and turns ON the endoscope system 1 to bring the respective sections into a start-up state. Both the processors 4A and 4B are set to the normal observation mode immediately after the start-up state.

Next, the user inserts the distal end portion 21A of the endoscope 2A into a body cavity, and then, continues to insert the insertion portion 22A until the distal end portion 21A reaches a desired observation region while watching an image displayed on the monitor 5A.

The endoscope 2A picks up an image of a diseased region 102 existing along one side of the body cavity wall 101, for example, as a subject by the image pickup section provided at the distal end portion 21A in the desired observation region, and outputs the image of the diseased region 102 as an image pickup signal.

On the other hand, the control section 43A detects that both the observation mode selector switch 44A and the observation mode selector switch 44B are OFF based on the output state of the instruction from the observation mode selector switch 44A and the ON-OFF signal outputted from the processor 4B immediately after the start-up state.

When detecting that both the observation mode selector switches 44A and 44B are OFF, the control section 43A does not control the light control section 41A. Therefore, the light control section 41A controls the illuminating section 31A such that the light intensity of the illuminating light supplied from the light source device 3A to the endoscope 2A becomes a predetermined standard light intensity appropriate for observation with white light.

The processor 4A generates a video signal corresponding to the image pickup signal outputted from the endoscope 2A, and outputs the video signal to the monitor 5A. Accordingly, the image of the diseased region 102 existing along one side of the body cavity wall 101 is displayed on the monitor 5A.

Also, the user inserts a distal end side of the rigid endoscope 21B of the endoscope 2B into the body cavity through an unillustrated trocar.

The endoscope 2B picks up an image of the other side of the body cavity wall 101, for example, as a subject by the image pickup device provided in the camera head 23B, and outputs the image of the other side of the body cavity wall 101 as an image pickup signal.

On the other hand, the control section 43B detects that both the observation mode selector switch 44A and the observation mode selector switch 44B are OFF based on the output state of the instruction from the observation mode selector switch 44B and the ON-OFF signal outputted from the processor 4A immediately after the start-up state of the endoscope system 1.

When detecting that both the observation mode selector switches 44A and 44B are OFF, the control section 43B does not control the light control section 41B. Therefore, the light control section 41B controls the illuminating section 31B such that the light intensity of the illuminating light supplied from the light source device 3B to the endoscope 2B becomes a predetermined standard light intensity appropriate for observation with white light. The light intensities of the illuminating light emitted from each of the illuminating section 31A and the illuminating section 31B in the normal observation mode are substantially the same as the predetermined standard light intensity described above.

The processor 4B generates a video signal corresponding to the image pickup signal outputted from the endoscope 2B, and outputs the video signal to the monitor 5B. Accordingly, the image of the other side of the body cavity wall 101 is displayed on the monitor 5B.

As shown in FIG. 2, when both the observation mode selector switches 44A and 44B are OFF, both the endoscope 2A and the endoscope 2B illuminate the subject by the illuminating light having the predetermined standard light intensity.

After that, when the user turns ON the observation mode selector switch 44B, the observation mode of the processor 4B is switched from the normal observation mode to the transmitted light observation mode.

When detecting that the observation mode selector switch 44B is turned ON, the control section 43B controls the light control section 41B to decrease the light intensity of the illuminating light supplied from the light source device 3B to the endoscope 2B. Also, the control section 43B outputs an ON-OFF signal for indicating that the observation mode selector switch 44B is turned ON to the processor 4A in addition to performing the above control.

Based on the control of the control section 431, the light control section 41B controls the illuminating section 31B to reduce the light intensity of the illuminating light supplied from the light source device 3B to the endoscope 2B to half the predetermined standard light intensity (described above), for example, as control for decreasing the light intensity of the illuminating light to a light intensity at which the body cavity wall 101 can be recognized.

Based on the control of the light control section 41B, the illuminating section 31B changes the aperture value of the unillustrated aperture such that the light intensity of the illuminating light supplied to the endoscope 2B is reduced to half the predetermined standard light intensity (described above).

On the other hand, the control section 43A disables the instruction from the observation mode selector switch 44A, and controls the light control section 41A to increase the light intensity of the illuminating light supplied from the light source device 3A to the endoscope 2A while the observation mode selector switch 44B is ON based on the ON-OFF signal from the processor 4B.

Based on the control of the control section 43A, the light control section 41A controls the illuminating section 31A to increase the light intensity of the illuminating light supplied from the light source device 3A to the endoscope 2A to twice the predetermined standard light intensity (described above), for example, as control for increasing the light intensity of the illuminating light to a light intensity relatively large in comparison with the predetermined standard light intensity (described above), and a light intensity at which at least one portion of the illuminating light is transmitted through the body cavity wall 101.

Based on the control of the light control section 41A, the illuminating section 31A changes the aperture value of the unillustrated aperture such that the light intensity of the illuminating light supplied to the endoscope 2A is increased to twice the predetermined standard light intensity (described above).

As described above, in the present embodiment, when the observation mode selector switch 44B is turned ON, the light intensity of the illuminating light emitted from the distal end portion 21A disposed at one side of the body cavity wall 101 is increased. Accordingly, a position of the diseased region 102 can be easily found even from the other side of the body cavity wall 101. As a result, when performing treatment of the diseased region 102 by using the endoscope 2B and an unillustrated treatment instrument or the like while performing observation or the like by using the endoscope 2A, the user can perform the treatment more smoothly than before.

When the processor 4B is in the transmitted light observation mode, the user may change the light intensity of the illuminating light supplied from the light source device 3B to the endoscope 2B within a range in which the position of the diseased region 102 (distal end portion 21A) can be visually recognized and in which the body cavity wall 101 can be visually recognized, for example, by operating the transmitted light intensity adjusting switch 45B.

Also, when the user turns ON the observation mode selector switch 44A from the state in which both the observation mode selector switch 44A and the observation mode selector switch 44B are OFF, the observation mode of the processor 4A is switched from the normal observation mode to the transmitted light observation mode.

When detecting that the observation mode selector switch 44A is turned ON, the control section 43A controls the light control section 41A to decrease the light intensity of the illuminating light supplied from the light source device 3A to the endoscope 2A. Also, the control section 43A outputs an ON-OFF signal for indicating that the observation mode selector switch 44A is turned ON to the processor 4B in addition to performing the above control.

Based on the control of the control section 43A, the light control section 41A controls the illuminating section 31A to reduce the light intensity of the illuminating light supplied from the light source device 3A to the endoscope 2A to half the predetermined standard light intensity (described above), for example, as control for decreasing the light intensity of the illuminating light to a light intensity at which the body cavity wall 101 and the diseased region 102 can be recognized.

Based on the control of the light control section 41A, the illuminating section 31A changes the aperture value of the unillustrated aperture such that the light intensity of the illuminating light supplied to the endoscope 2A is reduced to half the predetermined standard light intensity (described above).

On the other hand, the control section 43B disables the instruction from the observation mode selector switch 44B, and controls the light control section 41B to increase the light intensity of the illuminating light supplied from the light source device 3B to the endoscope 2B while the observation mode selector switch 44A is ON based on the ON-OFF signal from the processor 4A.

Based on the control of the control section 43B, the light control section 41B controls the illuminating section 31B to increase the light intensity of the illuminating light supplied from the light source device 3B to the endoscope 2B to twice the predetermined standard light intensity (described above), for example, as control for increasing the light intensity of the illuminating light to a light intensity relatively large in comparison with the predetermined standard light intensity (described above), and a light intensity at which at least one portion of the illuminating light is transmitted through the body cavity wall 101.

Based on the control of the light control section 41B, the illuminating section 31B changes the aperture value of the unillustrated aperture such that the light intensity of the illuminating light supplied to the endoscope 2B is increased to twice the predetermined standard light intensity (described above).

As described above, in the present embodiment, when the observation mode selector switch 44A is turned ON, the light intensity of the illuminating light emitted from the rigid endoscope 21B disposed at the other side of the body cavity wall 101 is increased. Accordingly, a position where the distal end portion of the rigid endoscope 21B is disposed can be easily found even from one side of the body cavity wall 101. As a result, when performing observation or the like of the diseased region 102 by using the endoscope 2A while providing treatment by using the endoscope 2B and an unillustrated treatment instrument or the like, the user can perform the observation or the like more smoothly than before.

When the processor 4A is in the transmitted light observation mode, the user may change the light intensity of the illuminating light supplied from the light source device 3A to the endoscope 2A within a range in which the position of the distal end portion of the rigid endoscope 21B can be visually recognized and in which the body cavity wall 101 and the diseased region 102 can be visually recognized, for example, by operating the transmitted light intensity adjusting switch 45A.

Because of the action described above, the endoscope system 1 in the present embodiment enables a desired target region to be found more easily than before when the target region is observed by using the two endoscopes.

The endoscope system 1 in the present embodiment is not limited to one performing the operation and the control in the above action in order to obtain the above effects. For example, the endoscope system may perform operation and control as described below. For the simplicity of description, the following description will be made by appropriately omitting the same portions as those described above. Also, the action described below concerning FIG. 3 is about an example in which the observation mode selector switch 44A is turned OFF and the observation mode selector switch 44B is turned ON.

When both the observation mode selector switch 44A and the observation mode selector switch 44B are OFF, both the endoscope 2A and the endoscope 2B illuminate the subject by the illuminating light having the predetermined standard light intensity.

Also, when both the observation mode selector switches 44A and 44B are OFF, the image processing section 42A sequentially accumulates image pickup signals outputted from the endoscope 2A in the frame memory, and generates video signals corresponding to the image pickup signals to output the video signals to the monitor 5A. Also, when both the observation mode selector switches 44A and 44B are OFF, the image processing section 42B sequentially accumulates image pickup signals outputted from the endoscope 2B in the frame memory, and generates video signals corresponding to the image pickup signals to sequentially output the video signals to the monitor 5B.

In this state, when a user turns ON the observation mode selector switch 44B, the observation mode of the processor 4B is switched from the normal observation mode to the transmitted light observation mode. The control section 43B thereby outputs an ON-OFF signal for indicating that the observation mode selector switch 44B is turned ON to the processor 4A.

The control section 43A disables the instruction from the observation mode selector switch 44A, and controls the light control section 41A to increase the light intensity of the illuminating light supplied from the light source device 3A to the endoscope 2A while the observation mode selector switch 44B is ON based on the ON-OFF signal from the processor 4B.

Based on the control of the control section 43A, the light control section 41A controls the illuminating section 31A to output a pulse light whose light intensity is alternately switched between the predetermined standard light intensity (described above) and a light intensity exceeding the predetermined standard light intensity in every predetermined cycle as shown in FIG. 3, for example, as control for increasing the light intensity of the illuminating light supplied from the light source device 3A to the endoscope 2A to a light intensity relatively large in comparison with the predetermined standard light intensity (described above), and a light intensity at which at least one portion of the illuminating light is transmitted through the body cavity wall 101.

Based on the control of the light control section 41A, the illuminating section 31A appropriately changes the aperture value of the unillustrated aperture such that the above pulse light is supplied to the endoscope 2A.

Also, the control section 43A controls the image processing section 42A not to use an image of the subject obtained at a timing when the light having the light intensity exceeding the predetermined standard light intensity is emitted to the subject in generating the video signals, based on the predetermined cycle of the above pulse light.

The image processing section 42A does not accumulate in the frame memory the image of the subject obtained at the timing when the light having the light intensity exceeding the predetermined standard light intensity is emitted from the illuminating section 31A to the subject, and accumulates in the frame memory only an image of the subject obtained at a timing when the light having the predetermined standard light intensity is emitted from the illuminating section 31A to the subject to generate the video signals, based on the image pickup signals outputted from the endoscope 2A and the control of the control section 43A. A portion in FIG. 3 in which diagonal lines are drawn represents a subject image component which is not accumulated in the frame memory of the image processing section 42A (image processing section 42B) out of the image pickup signals outputted from the endoscope 2A (endoscope 2B).

That is, the image processing section 42A treats an image of the subject for one field obtained at the timing when the light having the predetermined standard light intensity is emitted from the illuminating section 31A to the subject as equivalent to images of the subject for two fields, and generates the video signals based on the image pickup signals accumulated in the unillustrated frame memory to output the video signals to the monitor 5A at a timing before or after the observation mode selector switch 44B is turned ON (or OFF) and while the observation mode selector switch 44B is ON as shown in FIG. 3. Accordingly, even in the transmitted light observation mode, an image of the subject (image of the body cavity wall 101 and the diseased region 102) having the same luminance as that of an image of the subject in the normal observation mode is displayed on the monitor 5A.

On the other hand, the control section 43B detects the content of control performed by the control section 43A and the light control section 41A after outputting the ON-OFF signal for indicating that the observation mode selector switch 44B is turned ON. When detecting that the control for outputting the above pulse light from the light source device 3A is performed, the control section 43B controls the image processing section 423 not to use an image of the subject obtained at the timing when the light having the predetermined standard light intensity is emitted from the illuminating section 31A to the subject in generating the video signals, based on the predetermined cycle of the above pulse light.

The image processing section 42B does not accumulate in the frame memory the image of the subject obtained at the timing when the light having the predetermined standard light intensity is emitted from the illuminating section 31A to the subject, and accumulates in the frame memory only an image of the subject obtained at the timing when the light having the light intensity exceeding the predetermined standard light intensity is emitted from the illuminating section 31A to the subject to generate the video signals, based on the image pickup signals outputted from the endoscope 2B and the control of the control section 43B.

That is, the image processing section 42B treats an image of the subject for one field obtained at the timing when the light having the light intensity exceeding the predetermined standard light intensity is emitted from the illuminating section 31A to the subject as equivalent to images of the subject for two fields, and generates the video signals based on the image pickup signals accumulated in the unillustrated frame memory to output the video signals to the monitor 5B while the observation mode selector switch 44B is ON as shown in FIG. 3. Accordingly, in the transmitted light observation mode, an image in which it is easy to visually recognize from which position in a body cavity a light being transmitted through the body cavity wall 101 is emitted is displayed on the monitor 5B. As a result, the user can easily find the position of (the distal end portion 21A and) the diseased region 102 disposed at one side of the body cavity wall 101 even from the other side of the body cavity wall 101 while watching the image displayed on the monitor 5B.

The control performed by the control section 43B on the image processing section 42B and the operation of the image processing section 42B corresponding to the control are not limited to those described above.

To be more specific, when detecting that the control for outputting the above pulse light from the light source device 3A is performed, the control section 43B may control the image processing section 42B to emphasize the image of the subject obtained at the timing when the light having the light intensity exceeding the predetermined standard light intensity is emitted from the illuminating section 31A to the subject and generate the video signals, based on the predetermined cycle of the pulse light.

In this case, the image processing section 42B of a present modification sequentially stores in the frame memory the image of the subject obtained at the timing when the light having the light intensity exceeding the predetermined standard light intensity is emitted from the illuminating section 31A to the subject, and the image of the subject obtained at the timing when the light having the predetermined standard light intensity is emitted from the illuminating section 31A to the subject. In other words, the image processing section 42B of the present modification accumulates the images of the subject for two fields, which are temporally successive, in the frame memory based on the image pickup signals outputted from the endoscope 213 in the transmitted light observation mode.

Then, the image processing section 42B first superimposes two fields of images of the subject obtained at the timing when the light having the light intensity exceeding the predetermined standard light intensity is emitted from the illuminating section 31A to the subject based on the images of the subject accumulated in the frame memory and the control of the control section 43B.

After that, the image processing section 42B performs a calculation to obtain a difference between the superimposed images of the subject for two fields and the image of the subject for one field obtained at the timing when the light having the predetermined standard light intensity is emitted from the illuminating section 31A to the subject, and generates and outputs the video signals corresponding to the image of the subject after the calculation. Accordingly, in the transmitted light observation mode, an image in which a position in a body cavity from which a light being transmitted through the body cavity wall 101 is emitted is emphasized is displayed on the monitor 5B. As a result, the user can easily find the position of (the distal end portion 21A and) the diseased region 102 disposed at one side of the body cavity wall 101 even from the other side of the body cavity wall 101 while watching the image displayed on the monitor 5B.

In the endoscope system 1 of the present embodiment, an illuminating treatment instrument 201 as shown in FIG. 4A enabling a user to easily recognize a size of the diseased region 102 existing in one side of the body cavity wall 101 from the other side of the body cavity wall 101 may be also used.

The illuminating treatment instrument 201 includes an illuminating treatment instrument body 202 that can be inserted into an unillustrated treatment instrument channel provided in the endoscope 2A and has substantially the same flexibility as that of the insertion portion 22A of the endoscope 2A, a sliding member 203 that is inserted into the illuminating treatment instrument body 202 and is slidable in a longitudinal direction of the illuminating treatment instrument body 202, and a lever 204 provided in a proximal end side of the sliding member 203 and capable of sliding the sliding member 203 by a pushing and pulling operation.

The illuminating treatment instrument body 202 includes a light source section 202a capable of emitting a light having a larger light intensity than the light intensity of the illuminating light emitted from the light source device 3A in the transmitted light observation mode at a distal end side.

Also, the sliding member 203 includes a light source section 203a capable of emitting a light having a larger light intensity than the light intensity of the illuminating light emitted from the light source device 3A in the transmitted light observation mode at a distal end side.

The light source sections 202a and 203a include a lamp or the like, for example, and emit a light by receiving power supply from an unillustrated secondary battery or the like that can be mounted on the illuminating treatment instrument body 202. In the present embodiment, the light source sections 202a and 203a are respectively configured to emit a white light having substantially the same light intensity.

Here, the action of the illuminating treatment instrument 201 having the configuration described above is simply described.

A user inserts the illuminating treatment instrument body 202 (and the sliding member 203) into the treatment instrument channel provided in the endoscope 2A, and then, projects the light source sections 202a and 203a from the distal end portion 21A as shown in FIG. 4B, for example. In the above state, the user slides the sliding member 203 while pushing or pulling the lever 204 (not shown in FIG. 4B) to dispose the diseased region 102 between the light source sections 202a and 203a.

At this time, the light source sections 202a and 203a emitting the light having the larger light intensity than the light intensity of the illuminating light emitted from the light source device 3A via the light guide inserted into the endoscope 2A in the transmitted light observation mode are disposed in portions corresponding to both end portions of the diseased region 102. Accordingly, the user can easily recognize the size of the diseased region 102 existing in one side of the body cavity wall 101 from the other side of the body cavity wall 101.

Second Embodiment

Figure 5:
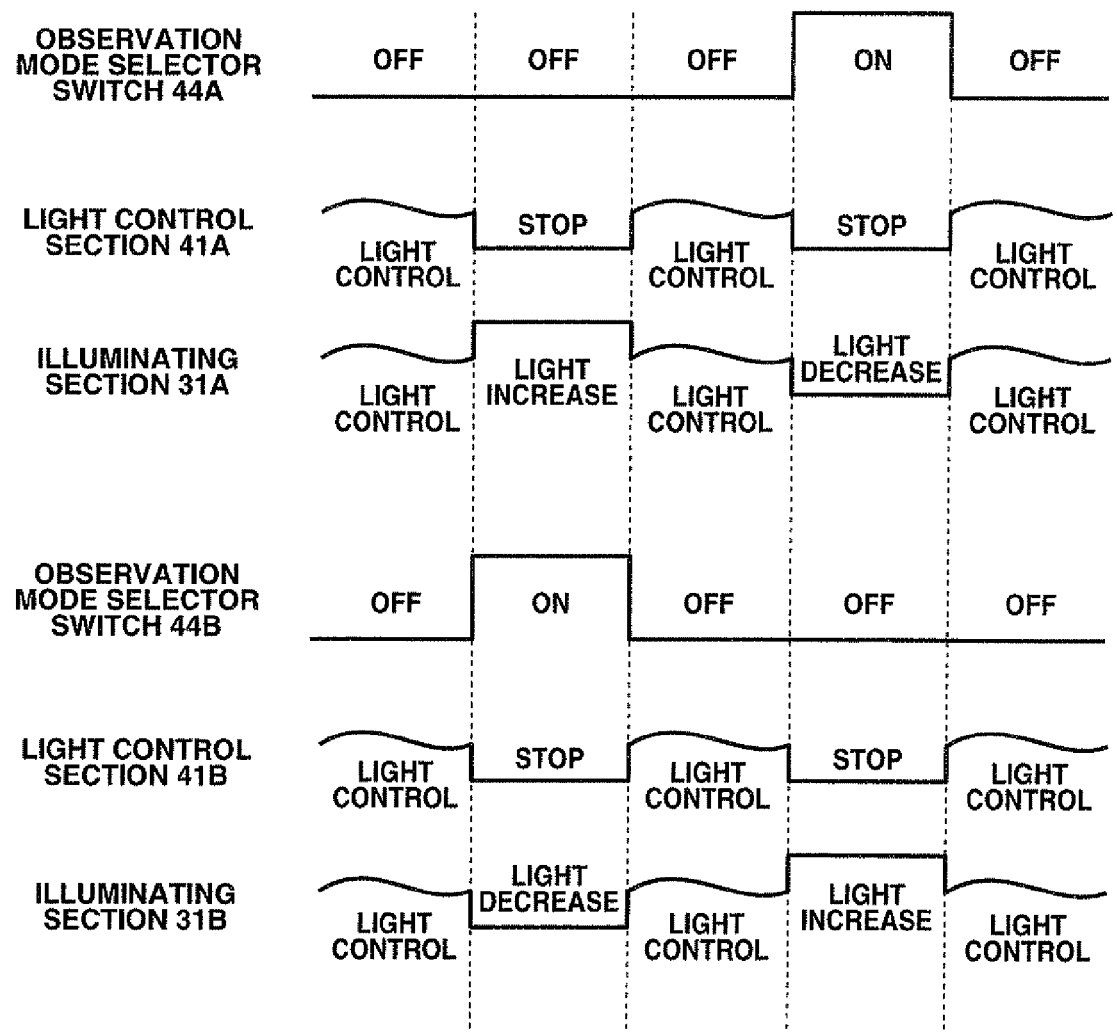
FIG. 5 illustrates an example of an operating state of each illuminating section and each light control section when one of observation mode selector switches is turned ON according to a second embodiment.

FIG. 5 is related to a second embodiment of the present invention. FIG. 5 illustrates an example of an operating state of each illuminating section and each light control section when one of observation mode selector switches is turned ON according to the second embodiment.

In the following description, the detailed description of portions having the same configurations as those of the first embodiment will be omitted. In the present embodiment, portions different from those of the first embodiment will be mainly described. Also, the endoscope system 1 of the present embodiment has the same configuration as that shown in FIG. 1 described above.

Here, the action of the endoscope system 1 of the present embodiment will be described.

When both the observation mode selector switch 44A and the observation mode selector switch 44B are OFF, that is, when the endoscope system 1 is set to the normal observation mode, the control section 43A of the processor 4A puts the light control section 41A into operation, and controls to appropriately adjust the light intensity of the illuminating light supplied from the illuminating section 31A of the light source device 3A to the endoscope 2A (to a predetermined light intensity, for example). Also, when the endoscope system 1 is set to the normal observation mode, the control section 43B of the processor 4B puts the light control section 41B into operation, and controls to appropriately adjust the light intensity of the illuminating light supplied from the illuminating section 31B of the light source device 3B to the endoscope 2B (to a predetermined light intensity, for example).

After that, when a user turns ON the observation mode selector switch 44B, the observation mode of the processor 4B is switched from the normal observation mode to the transmitted light observation mode.

When detecting that the observation mode selector switch 44B is turned ON, the control section 43B performs control such that the light intensity of the illuminating light supplied from the illuminating section 31B of the light source device 3B to the endoscope 2B is reduced to be relatively small in comparison with the illuminating light supplied from the illuminating section 31A of the light source device 3A to the endoscope 2A by stopping the operation of the light control section 41B and decreasing the light intensity of the illuminating light supplied from the illuminating section 31B of the light source device 3B to the endoscope 2B. Also, the control section 43B outputs an ON-OFF signal for indicating that the observation mode selector switch 44B is turned ON to the processor 4A in addition to performing the above control.

On the other hand, the control section 43A disables the instruction from the observation mode selector switch 44A and stops the operation of the light control section 41A while the observation mode selector switch 44B is ON based on the ON-OFF signal from the processor 4B. Then, the control section 43A performs control such that the light intensity of the illuminating light supplied from the illuminating section 31A of the light source device 3A to the endoscope 2A can be transmitted through a body cavity wall and is relatively large in comparison with the illuminating light supplied from the illuminating section 31B of the light source device 3B to the endoscope 2B by increasing the light intensity of the illuminating light supplied from the illuminating section 31A of the light source device 3A to the endoscope 2A.

As described above, in the present embodiment, when the observation mode selector switch 44B is turned ON, the operations of the light control sections 41A and 41B are stopped. Also, the light intensity of the illuminating light emitted from the distal end portion 21A disposed at one side of the body cavity wall 101 is increased, and the light intensity of the illuminating light emitted from the distal end portion 21B disposed at the other side of the body cavity wall 101 is decreased. Accordingly, in the present embodiment, the position of the diseased region 102 can be easily found even from the other side. As a result, when performing treatment of the diseased region 102 by using the endoscope 2B and an unillustrated treatment instrument or the like while performing observation or the like by using the endoscope 2A, the user can perform the treatment more smoothly than before.

On the other hand, when the user turns ON the observation mode selector switch 44A from the state in which both the observation mode selector switch 44A and the observation mode selector switch 44B are OFF, the observation mode of the processor 4A is switched from the normal observation mode to the transmitted light observation mode.

When detecting that the observation mode selector switch 44A is turned ON, the control section 43A performs control such that the light intensity of the illuminating light supplied from the illuminating section 31A of the light source device 3A to the endoscope 2A is reduced to be relatively small in comparison with the illuminating light supplied from the illuminating section 31B of the light source device 3B to the endoscope 2B by stopping the operation of the light control section 41A and decreasing the light intensity of the illuminating light supplied from the illuminating section 31A of the light source device 3A to the endoscope 2A. Also, the control section 43A outputs an ON-OFF signal for indicating that the observation mode selector switch 44A is turned ON to the processor 4B in addition to performing the above control.

The control section 43B disables the instruction from the observation mode selector switch 44B and stops the operation of the light control section 41B while the observation mode selector switch 44A is ON based on the ON-OFF signal from the processor 4A. Then, the control section 43B performs control such that the light intensity of the illuminating light supplied from the illuminating section 31B of the light source device 3B to the endoscope 2B can be transmitted through a body cavity wall and is relatively large in comparison with the illuminating light supplied from the illuminating section 31A of the light source device 3A to the endoscope 2A by increasing the light intensity of the illuminating light supplied from the illuminating section 31B of the light source device 3B to the endoscope 2B.

As described above, in the present embodiment, when the observation mode selector switch 44A is turned ON, the operations of the light control sections 41A and 41B are stopped. Also, the light intensity of the illuminating light emitted from the distal end portion 21B disposed at one side of the body cavity wall 101 is increased, and the light intensity of the illuminating light emitted from the distal end portion 21A disposed at the other side of the body cavity wall 101 is decreased. Accordingly, in the present embodiment, the position of the diseased region 102 can be easily found even from the other side. As a result, when performing observation or the like of the diseased region 102 by using the endoscope 2A while providing treatment by using the endoscope 2B and an unillustrated treatment instrument or the like, the user can perform the observation or the like more smoothly than before.

Because of the action described above, the endoscope system 1 in the present embodiment enables a desired target region to be found more easily than before when the target region is observed by using the two endoscopes.

Third Embodiment

Figure 6:
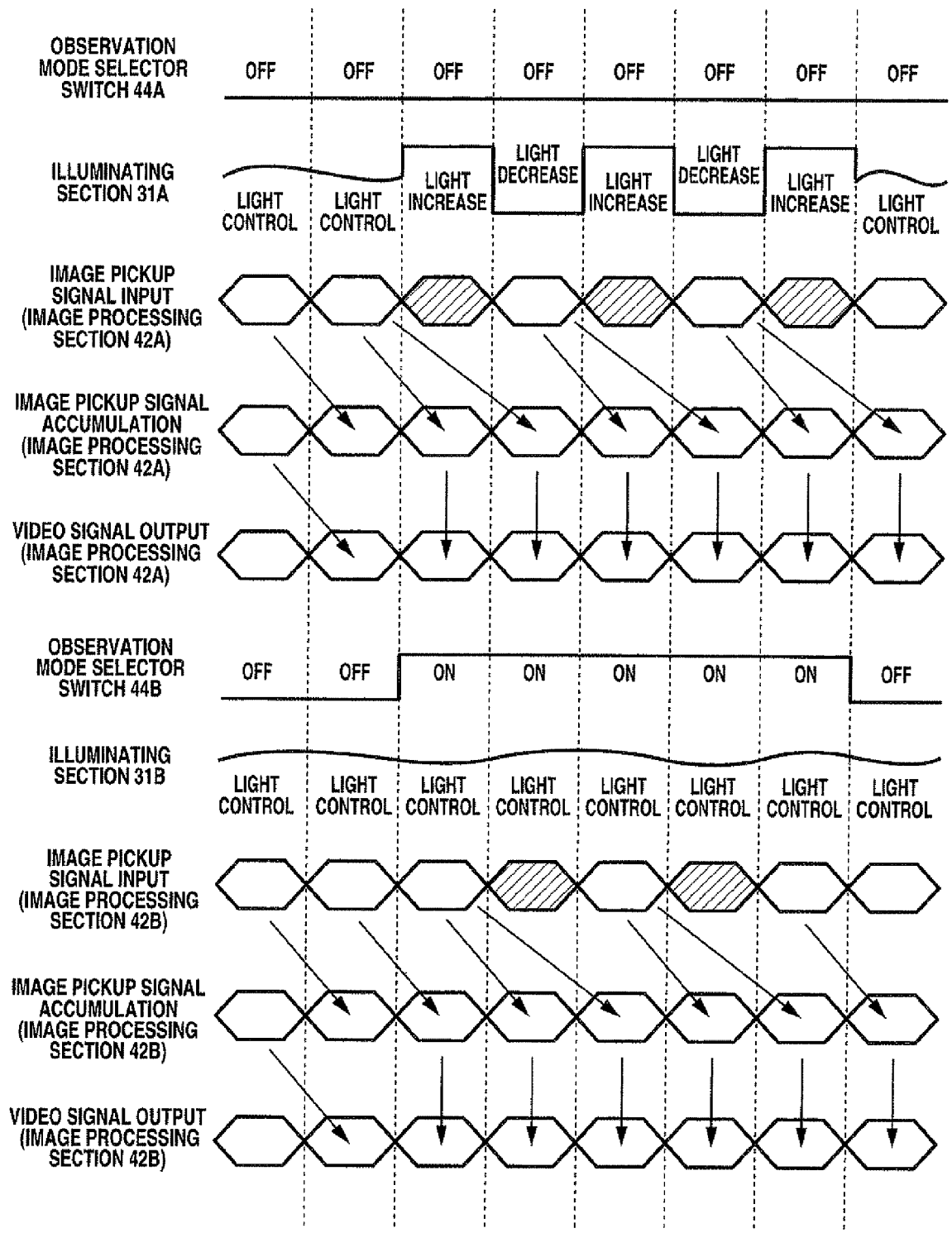
FIG. 6 illustrates an example of an operating state of each illuminating section and each image processing section when one of observation mode selector switches is turned ON according to a third embodiment.

FIG. 6 is related to a third embodiment of the present invention. FIG. 6 illustrates an example of operating states of each illuminating section and each image processing section when one of observation mode selector switches is turned ON according to the third embodiment.

In the following description, the detailed description of portions having the same configurations as those of the first and second embodiments will be omitted. In the present embodiment, portions different from those of the first and second embodiments will be mainly described. Also, the endoscope system 1 of the present embodiment has the same configuration as that shown in FIG. 1 described above.

Here, the action of the endoscope system 1 of the present embodiment will be described.

When both the observation mode selector switch 44A and the observation mode selector switch 44B are OFF, that is, when the endoscope system 1 is set to the normal observation mode, both the light control section 41A and the light control section 41B are in operation.

Accordingly, when the endoscope system 1 is set to the normal observation mode, an illuminating light which is being controlled by the light control section 41A is supplied to the endoscope 2A, and an illuminating light which is being controlled by the light control section 41B is supplied to the endoscope 2B.

Also, when both the observation mode selector switches 44A and 44B are OFF, the image processing section 42A accumulates image pickup signals outputted from the endoscope 2A one field by one field in the frame memory, and generates and outputs video signals based on the accumulated image pickup signals to the monitor 5A. Also, when both the observation mode selector switches 44A and 44B are OFF, the image processing section 42B accumulates image pickup signals outputted from the endoscope 2B one field by one field in the frame memory, and generates and outputs video signals based on the accumulated image pickup signals to the monitor 5B.

In this state, when a user turns ON the observation mode selector switch 44B, the observation mode of the processor 4B is switched from the normal observation mode to the transmitted light observation mode. The control section 43B thereby outputs an ON-OFF signal for indicating that the observation mode selector switch 44B is turned ON to the processor 4A.

The control section 43A disables the instruction from the observation mode selector switch 44A and stops the operation of the light control section 41A while the observation mode selector switch 44B is ON based on the ON-OFF signal from the processor 4B. Then, the control section 43A controls to emit the illuminating light supplied from the illuminating section 31A of the light source device 3A to the endoscope 2A as a pulse light which is alternately switched between a light having a light intensity large enough to transmit the light through the body cavity wall 101 and a light having a light intensity not large enough to transmit the light through the body cavity wall 101 in every predetermined cycle.

Also, the control section 43A controls the image processing section 42A not to use an image of a subject obtained at a timing when the light having the light intensity large enough to transmit the light through the body cavity wall 101 is emitted to the subject (timing of "light increase" in FIG. 6) in generating the video signals, based on the predetermined cycle of the above pulse light.

The image processing section 42A does not accumulate in the frame memory the image of the subject obtained at the timing when the light having the light intensity large enough to transmit the light through the body cavity wall 101 is emitted from the illuminating section 31A to the subject (timing of "light increase" in FIG. 6), and accumulates in the frame memory only an image of the subject obtained at a timing when the light having the light intensity not large enough to transmit the light through the body cavity wall 101 is emitted from the illuminating section 31A to the subject (timing of "light decrease" in FIG. 6) to generate the video signals, based on the image pickup signals outputted from the endoscope 2A and the control of the control section 43A. A portion in FIG. 6 in which diagonal lines are drawn represents a subject image component which is not accumulated in the frame memory of the image processing section 42A (image processing section 42B) out of the image pickup signals outputted from the endoscope 2A (endoscope 2B).

That is, the image processing section 42A treats an image of the subject for one field obtained at the timing indicated as "light decrease" as equivalent to images of the subject for two fields, and generates the video signals based on the image pickup signals accumulated in the unillustrated frame memory to output the video signals to the monitor 5A at a timing before or after the observation mode selector switch 44B is turned ON (or OFF) and while the observation mode selector switch 44B is ON as shown in FIG. 6. Accordingly, in the transmitted light observation mode, an image of the subject (image of the body cavity wall 101 and the diseased region 102) having a luminance appropriate for observation is displayed on the monitor 5A.

On the other hand, the control section 43B detects the content of control performed by the control section 43A and the light control section 41A after outputting the ON-OFF signal for indicating that the observation mode selector switch 44B is turned ON. When detecting that the control for outputting the above pulse light from the light source device 3A is performed, the control section 43B controls the image processing section 42B not to use an image of the subject obtained at the timing when the light having the light intensity not large enough to transmit the light through the body cavity wall 101 is emitted from the illuminating section 31A to the subject (timing of "light decrease" in FIG. 6) in generating the video signals, based on the predetermined cycle of the above pulse light.

The image processing section 42B does not accumulate in the frame memory the image of the subject obtained at the timing when the light having the light intensity not large enough to transmit the light through the body cavity wall 101 is emitted from the illuminating section 31A to the subject (timing of "light decrease" in FIG. 6), and accumulates in the frame memory only an image of the subject obtained at the timing when the light having the light intensity large enough to transmit the light through the body cavity wall 101 is emitted from the illuminating section 31A to the subject (timing of "light increase" in FIG. 6) to generate the video signals, based on the image pickup signals outputted from the endoscope 2B and the control of the control section 43B.

That is, the image processing section 42B treats an image of the subject for one field obtained at the timing indicated as "light increase" as equivalent to images of the subject for two fields, and generates the video signals based on the image pickup signals accumulated in the unillustrated frame memory to output the video signals to the monitor 5B while the observation mode selector switch 44B is ON as shown in FIG. 6. Accordingly, in the transmitted light observation mode, an image in which it is easy to visually recognize from which position in a body cavity the light having the light intensity large enough to transmit the light through the body cavity wall 101 is emitted is displayed on the monitor 5B. As a result, the user can easily find the position of (the distal end portion 21A and) the diseased region 102 disposed at one side of the body cavity wall 101 even from the other side of the body cavity wall 101 while watching the image displayed on the monitor 5B.

Fourth Embodiment

Figure 7:
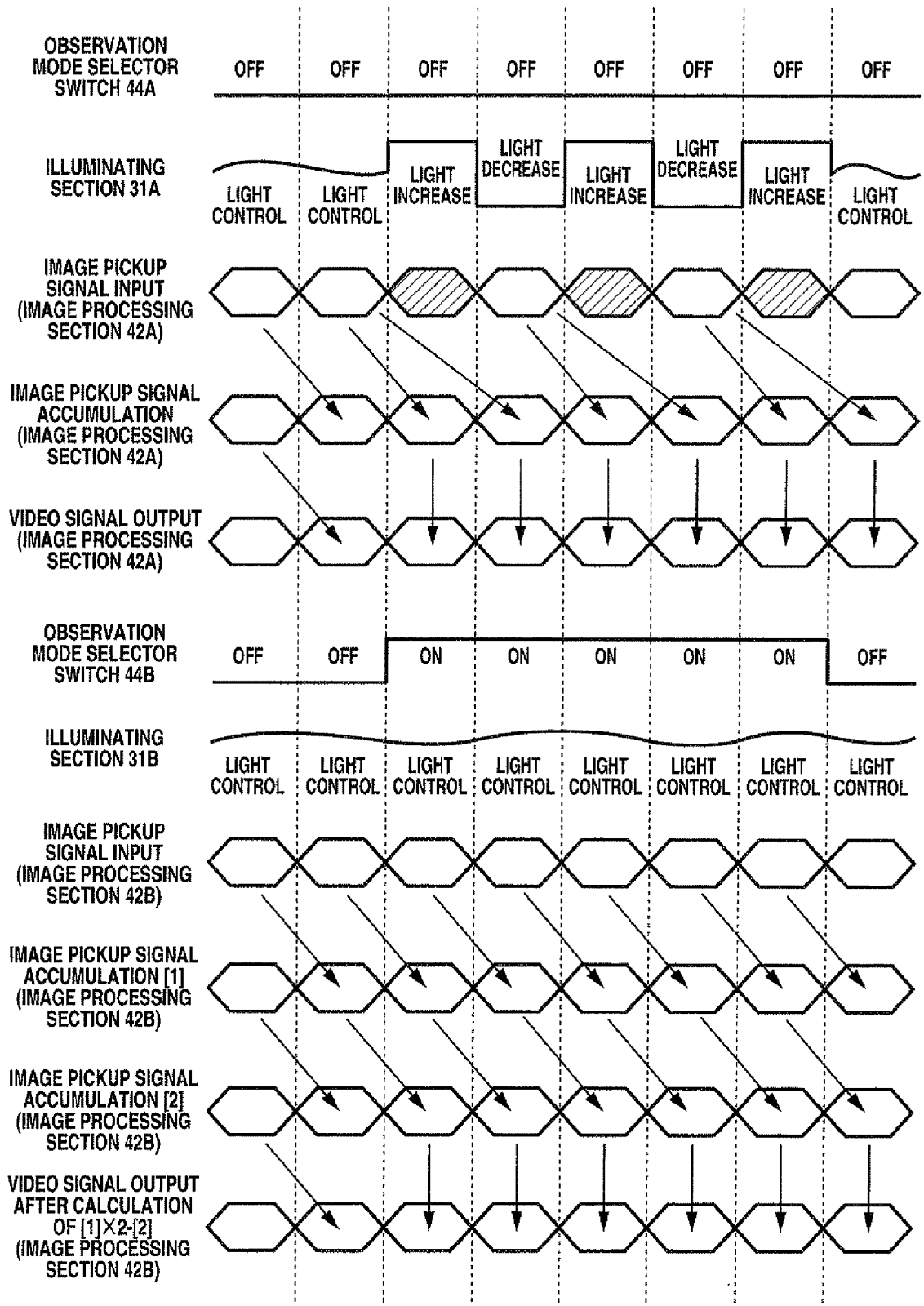
FIG. 7 illustrates an example of an operating state of each illuminating section and each image processing section when one of observation mode selector switches is turned ON according to a fourth embodiment.

FIG. 7 is related to a fourth embodiment of the present invention. FIG. 7 illustrates an example of an operating state of each illuminating section and each image processing section when one of observation mode selector switches is turned ON according to the fourth embodiment.

In the following description, the detailed description of portions having the same configurations as those of the first, second and third embodiments will be omitted. In the present embodiment, portions different from those of the first, second and third embodiments will be mainly described. Also, the endoscope system 1 in the present embodiment has the same configuration as that shown in FIG. 1 described above.

Here, the action of the endoscope system 1 of the present embodiment will be described. The description of the operation when the endoscope system 1 of the present embodiment is set to the normal observation mode will be omitted in the following since the operation is already described in the third embodiment or the like.

When the endoscope system 1 is in the normal observation mode, a user turns ON the observation mode selector switch 44B, and the observation mode of the processor 4B is switched from the normal observation mode to the transmitted light observation mode. The control section 43B thereby outputs an ON-OFF signal for indicating that the observation mode selector switch 44B is turned ON to the processor 4A.

Each section of the processor 4A performs substantially the same operation as that described in the third embodiment based on the ON-OFF signal from the processor 4B. That is, in accordance with the input of the ON-OFF signal from the processor 4B, the instruction from the observation mode selector switch 44A is disabled and the operation of the light control section 41A is stopped. Also, the control for emitting the illuminating light supplied from the illuminating section 31A to the endoscope 2A is performed as the pulse light described in the third embodiment.

Also, the control section 43A controls the image processing section 42A not to use an image of a subject obtained at a timing when the light having the light intensity large enough to transmit the light through the body cavity wall 101 is emitted to the subject (timing of "light increase" in FIG. 7) in generating the video signals, based on the predetermined cycle of the above pulse light.

The image processing section 42A does not accumulate in the frame memory the image of the subject obtained at the timing when the light having the light intensity large enough to transmit the light through the body cavity wall 101 is emitted from the illuminating section 31A to the subject (timing of "light increase" in FIG. 7), and accumulates in the frame memory only an image of the subject obtained at a timing when the light having the light intensity not large enough to transmit the light through the body cavity wall 101 is emitted from the illuminating section 31A to the subject (timing of "light decrease" in FIG. 7) to generate the video signals, based on the image pickup signals outputted from the endoscope 2A and the control of the control section 43A. A portion in FIG. 7 in which diagonal lines are drawn represents a subject image component which is not accumulated in the frame memory of the image processing section 42A out of the image pickup signals outputted from the endoscope 2A.

That is, the image processing section 42A treats an image of the subject for one field obtained at the timing indicated as "light decrease" as equivalent to images of the subject for two fields, and generates the video signals based on the image pickup signals accumulated in the unillustrated frame memory to output the video signals to the monitor 5A at a timing before or after the observation mode selector switch 44B is turned ON (or OFF) and while the observation mode selector switch 44B is ON as shown in FIG. 7. Accordingly, in the transmitted light observation mode, an image of the subject (image of the body cavity wall 101 and the diseased region 102) having a luminance appropriate for observation is displayed on the monitor 5A.

On the other hand, the control section 43B detects the content of control performed by the control section 43A and the light control section 41A after outputting the ON-OFF signal for indicating that the observation mode selector switch 44B is turned ON. When detecting that the control for outputting the above pulse light from the light source device 3A is performed, the control section 43B controls the image processing section 42B to emphasize an image of the subject obtained at the timing when the light having the light intensity large enough to transmit the light through the body cavity wall 101 is emitted from the illuminating section 31A to the subject (timing of "light increase" in FIG. 7) and generate the video signals, based on the predetermined cycle of the above pulse light.

In this case, the image processing section 42B of the present embodiment sequentially stores in the frame memory the image of the subject obtained at the timing when the light having the light intensity large enough to transmit the light through the body cavity wall 101 is emitted to the subject (timing of "light increase" in FIG. 7), and an image of the subject obtained at the timing when the light having the light intensity not large enough to transmit the light through the body cavity wall 101 is emitted from the illuminating section 31A to the subject (timing of "light decrease" in FIG. 7). In other words, the image processing section 42B of the present embodiment accumulates the images of the subject for two fields, which are temporally successive, in the frame memory based on the image pickup signals outputted from the endoscope 2B in the transmitted light observation mode.

Then, the image processing section 42B first superimposes two fields of images of the subject obtained at the timing when the light having the light intensity large enough to transmit the light through the body cavity wall 101 is emitted from the illuminating section 31A to the subject (timing of "light increase" in FIG. 7) based on the images of the subject accumulated in the frame memory and the control of the control section 43B.

After that, the image processing section 42B performs a calculation to obtain a difference between the superimposed images of the subject for two fields and the image of the subject for one field obtained at the timing when the light having the light intensity not large enough to transmit the light through the body cavity wall 101 is emitted from the illuminating section 31A to the subject (timing of "light decrease" in FIG. 7), and generates and outputs the video signals corresponding to the image of the subject after the calculation. Accordingly, in the transmitted light observation mode, an image in which a position in a body cavity from which the light being transmitted through the body cavity wall 101 is emitted is emphasized is displayed on the monitor 5B. As a result, the user can easily find the position of (the distal end portion 21A and) the diseased region 102 disposed at one side of the body cavity wall 101 even from the other side of the body cavity wall 101 while watching the image displayed on the monitor 5B.

The present invention is not limited to the respective embodiments described above, and various changes and applications can be made therein without departing from the scope of the invention.

What is claimed is:

1. An endoscope system comprising:
   a first endoscope including a first image pickup section capable of picking up an image of a subject;
   a first illuminating section capable of emitting a first illuminating light for illuminating the subject, the image of which is picked up by the first image pickup section;
   a second endoscope including a second image pickup section capable of picking up an image of the subject illuminated by the first illuminating light from a direction different from that of the first image pickup section;
   a second illuminating section capable of emitting a second illuminating light for illuminating the subject, the image of which is picked up by the second image pickup section;
   a video signal processing section for the second endoscope for generating a video signal for the second endoscope based on a signal picked up by the second image pickup section;
   a display section for the second endoscope for displaying an image of the subject obtained based on the video signal processing section for the second endoscope;

an emphasis instructing section for instructing an emphasis on an image obtained by the first illuminating light; and a video signal generation control section for performing, on the video signal processing section for the second endoscope, control to generate the video signal by not using the image of the subject obtained at a timing when light not having a light intensity large enough to transmit the light through the body cavity wall is emitted and by using, as images of the subject for two fields, an image of the subject for one field obtained at a timing when the light having the light intensity large enough to transmit the light through the body cavity wall is emitted based on a cycle of pulse emission in the first illuminating light.

2. An endoscope system comprising:

a first endoscope including a first image pickup section capable of picking up an image of a subject;

a first illuminating section capable of emitting a first illuminating light for illuminating the subject, the image of which is picked up by the first image pickup section;

a second endoscope including a second image pickup section capable of picking up an image of the subject illuminated by the first illuminating light from a direction different from that of the first image pickup section;

a second illuminating section capable of emitting a second illuminating light for illuminating the subject, the image of which is picked up by the second image pickup section;

a video signal processing section for the second endoscope for generating a video signal for the second endoscope based on a signal picked up by the second image pickup section;

a display section for the second endoscope for displaying an image of the subject obtained based on the video signal processing section for the second endoscope;

an emphasis instructing section for instructing an emphasis on an image obtained by the first illuminating light; and a video signal generation control section for performing, on the video signal processing section for the second endoscope, control to generate the video signal by performing a processing to superimpose images of the subject for two fields which are temporally successive, and further performing a calculating to obtain a difference between the image of the subject subjected to the processing and an image of the subject for one field obtained at a timing when light not having a light intensity large enough to transmit the light through the body cavity wall is emitted after the processing, based on a cycle of pulse emission in the first illuminating light.

* * * * *